United States Patent [19]
Toda et al.

[11] Patent Number: 5,442,592
[45] Date of Patent: Aug. 15, 1995

[54] ULTRASONIC DISTANCE METER

[75] Inventors: Minoru Toda, Lawrenceville, N.J.; Kyung T. Park, Berwyn, Pa.

[73] Assignee: The Whitaker Corporation, Wilmington, Del.

[21] Appl. No.: 193,345

[22] Filed: Feb. 8, 1994

[51] Int. Cl.[6] .................. G01S 11/14; G01N 29/00
[52] U.S. Cl. ..................... 367/124; 367/902; 73/861.18; 73/861.27
[58] Field of Search ........ 367/902, 118, 124; 73/861.28, 861.27, 861.18, 861.01

[56] References Cited

U.S. PATENT DOCUMENTS

| | | | |
|---|---|---|---|
| 3,100,885 | 8/1963 | Welkowitz et al. | 367/902 |
| 3,115,615 | 12/1963 | Saper | 367/902 |
| 3,237,150 | 2/1966 | Beck et al. | 367/902 |
| 4,064,742 | 12/1977 | Pittaro | 73/611 |
| 4,413,517 | 11/1983 | Soden | 73/597 |
| 4,437,332 | 3/1984 | Pittaro | 73/1 DV |
| 4,584,676 | 4/1986 | Newman | 367/108 |
| 4,658,648 | 4/1987 | Roddeck et al. | 73/597 |
| 4,715,008 | 12/1987 | Jones | 364/563 |
| 4,752,917 | 6/1988 | DeChape | 367/125 |
| 4,938,066 | 7/1990 | Dorr | 73/597 |
| 4,976,149 | 12/1990 | Ichikawa et al. | 73/597 |
| 5,095,754 | 3/1992 | Hsu et al. | 73/602 |
| 5,140,859 | 8/1992 | Shah | 73/597 |
| 5,163,323 | 11/1992 | Davidson | 73/290 V |
| 5,166,910 | 11/1992 | Batzle et al. | 367/191 |
| 5,181,778 | 1/1993 | Beller | 374/119 |
| 5,237,873 | 8/1993 | Eichenlaub | 73/597 |
| 5,255,564 | 10/1993 | Glad et al. | 73/597 |
| 5,341,345 | 8/1994 | Warner et al. | 367/99 |

*Primary Examiner*—Ian J. Lobo
*Attorney, Agent, or Firm*—Kevin D. McCarthy

[57] ABSTRACT

An ultrasonic distance meter cancels out the effects of temperature and humidity variations by including a measuring unit and a reference unit. In each of the units, a repetitive series of pulses is generated, each having a repetition rate directly related to the respective distance between an electroacoustic transmitter and an electroacoustic receiver. The pulse trains are provided to respective counters, and the ratio of the counter outputs is utilized to determine the distance being measured.

8 Claims, 1 Drawing Sheet

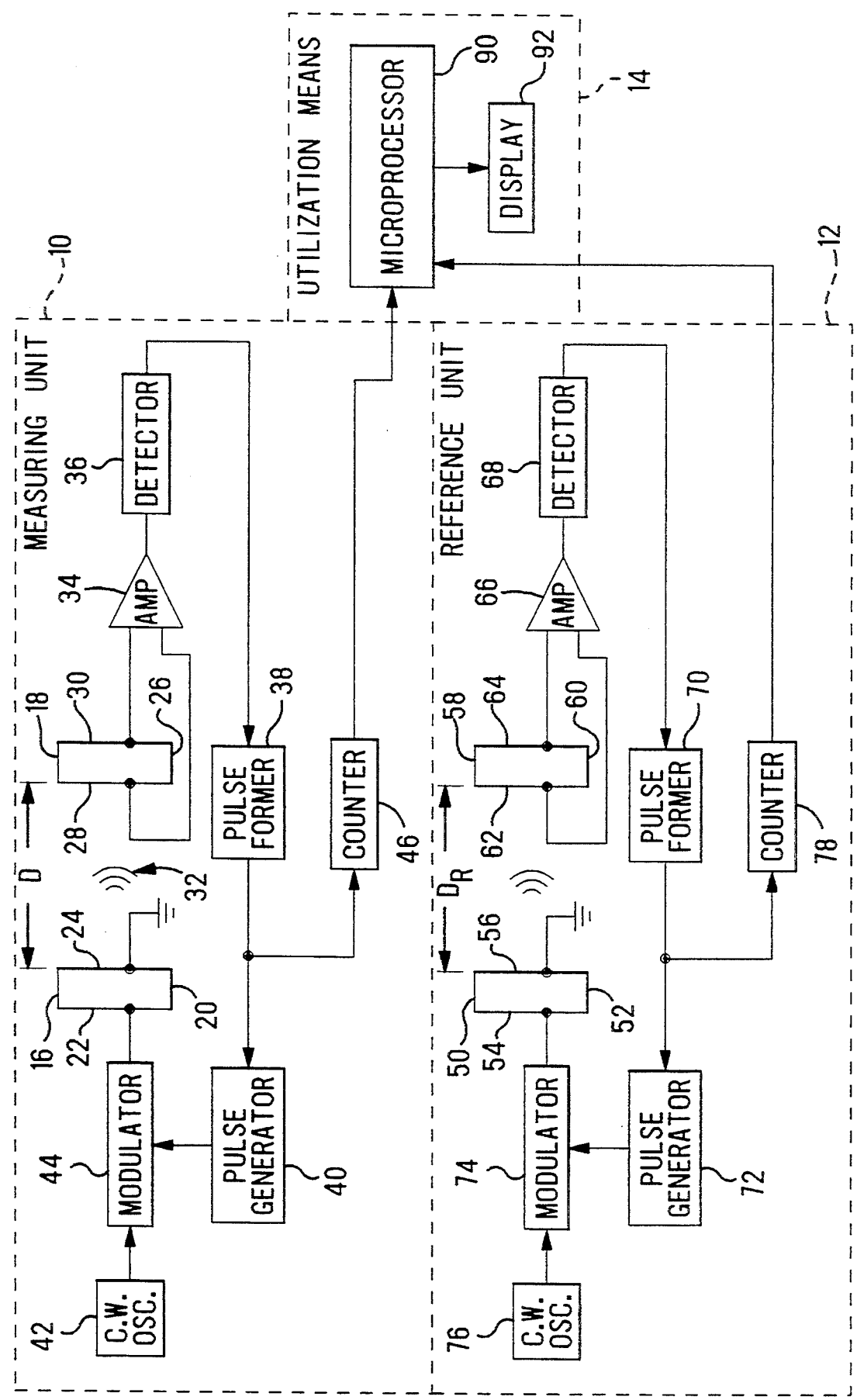

ULTRASONIC DISTANCE METER

BACKGROUND OF THE INVENTION

This invention relates to apparatus for the measurement of distance and, more particularly, to such apparatus which transmits ultrasonic waves between two points.

Precision machine tools must be calibrated. In the past, this has been accomplished utilizing mechanical devices such as calipers, micrometers, and the like. However, the use of such devices does not readily lend itself to automation techniques. It is known that the distance between two points can be determined by measuring the propagation time of a wave travelling between those two points. One such type of wave is an ultrasonic, or acoustic, wave. When an ultrasonic wave travels between two points, the distance between the two points can be measured by multiplying the transit time of the wave by the wave velocity in the medium separating the two points. It is therefore an object of the present invention to provide apparatus utilizing ultrasonic waves to accurately measure the distance between two points.

When the medium between the two points whose spacing is being measured is air, the sound velocity is dependent upon the temperature and humidity of the air. It is therefore a further object of the present invention to provide apparatus of the type described which is independent of temperature and humidity variations.

SUMMARY OF THE INVENTION

The foregoing and additional objects are attained in accordance with the principles of this invention by providing distance measuring apparatus which includes a reference unit and a measuring unit. The reference and measuring units are the same and each includes an electroacoustic transmitter and an electroacoustic receiver. The spacing between the transmitter and the receiver of the reference unit is a fixed reference distance, whereas the spacing between the transmitter and receiver of the measuring unit is the distance to be measured. In each of the units, the transmitter and receiver are coupled by a feedback loop which causes the transmitter to generate an acoustic pulse which is received by the receiver and converted into an electrical pulse which is then fed back to the transmitter, so that a repetitive series of pulses results. The repetition rate of the pulses is inversely related to the distance between the transmitter and the receiver. In each of the units, the pulses are provided to a counter. Since the reference distance is known, the ratio of the counter outputs is utilized to determine the desired distance to be measured. Since both counts are identically influenced by temperature and humidity variations, by taking the ratio of the counts, the resultant measurement becomes insensitive to such variations.

BRIEF DESCRIPTION OF THE DRAWINGS

The foregoing will be more readily apparent upon reading the following description in conjunction with the drawing in which the single FIGURE schematically depicts apparatus constructed in accordance with the principles of this invention.

DETAILED DESCRIPTION

Referring now to the drawing, there is shown a measuring unit 10 and a reference unit 12, both coupled to a utilization means 14. The measuring unit 10 includes an electroacoustic transmitter 16 and an electroacoustic receiver 18. The transmitter 16 includes piezoelectric material 20 sandwiched between a pair of electrodes 22 and 24. Likewise, the receiver 18 includes piezoelectric material 26 sandwiched between a pair of electrodes 28 and 30. As is known, by applying an electric field across the electrodes 22 and 24, stress is induced in the piezoelectric material 20. If the field varies, such as by the application of an electrical pulse, an acoustic wave 32 is generated. As is further known, when an acoustic wave impinges upon the receiver 18, this induces stress in the piezoelectric material 26 which causes an electrical signal to be generated across the electrodes 28 and 30. Although piezoelectric transducers have been illustrated, other electroacoustic devices may be utilized, such as, for example, electrostatic, electret or electromagnetic types.

As shown, the electrodes 28 and 30 of the receiver 18 are coupled to the input of an amplifier 34, whose output is coupled to the input of a detector 36. The detector 36 is arranged to provide a signal to the pulse former 38 when the output from the amplifier 34 exceeds a predetermined level. The pulse former 38 then generates a trigger pulse which is provided to the pulse generator 40. In order to enhance the sensitivity of the system, the transducers 16 and 18 are resonantly excited. There is accordingly provided a continuous wave oscillator 42 which provides a continuous oscillating signal at a fixed frequency, preferably the resonant frequency of the transducers 16 and 18. This oscillating signal is provided to the modulator 44. To effectively excite the transmitter 16, it is preferable to provide several cycles of the resonant frequency signal, rather than a single pulse or single cycle. Accordingly, the pulse generator 40 is arranged, in response to the application thereto of a trigger pulse, to provide a control pulse to the modulator 44 having a time duration equal the time duration of a predetermined number of cycles of the oscillating signal from the oscillator 42. This control pulse causes the modulator 44 to pass a "burst" of cycles to excite the transmitter 16.

When electric power is applied to the described circuitry, there is sufficient noise at the input to the amplifier 34 that its output triggers the pulse generator 40 to cause a burst of oscillating cycles to be provided across the electrodes 22 and 24 of the transmitter 16. The transmitter 16 accordingly generates an acoustic wave 32 which impinges upon the receiver 18. The receiver 18 then generates an electrical pulse which is applied to the input of the amplifier 34, which again causes triggering of the pulse generator 40. This cycle repeats itself so that a repetitive series of trigger pulses results at the output of the pulse former 38. This pulse train is applied to the counter 46, as well as to the pulse generator 40.

The transmitter 16 and the receiver 18 are spaced apart by the distance "D" which it is desired to measure. The propagation time "t" for an acoustic wave 32 travelling between the transmitter 16 and the receiver 18 is given by:

$$t = D/V_s$$

where $V_s$ is the velocity of sound in the air between the transmitter 16 and the receiver 18. The counter 46 measures the repetition rate of the trigger pulses, which is equal to $1/t$. Therefore, the repetition rate is equal to $V_s/D$. The velocity of sound in air is a function of the temperature and humidity of the air, as follows:

$$V_s = 331.45 \sqrt{(T + 273)/273} \; / \sqrt{1 - p(\Gamma_w/\Gamma_a - 0.622)/H}$$

where T is the temperature, p is the partial pressure of the water vapor, H is the barometric pressure, $\Gamma_w$ and $\Gamma_a$ are the ratio of constant pressure specific heat to constant volume specific heat for water vapor and dry air, respectively. Thus, although the repetition rate of the trigger pulses is measured very accurately by the counter 46, the sound velocity is influenced by temperature and humidity so that the measured distance D cannot be determined accurately.

In accordance with the principles of this invention, a reference unit 12 is provided. The reference unit 12 is of the same construction as the measuring unit 10 and therefore includes an electroacoustic transmitter 50 which includes piezoelectric material 52 sandwiched between a pair of electrodes 54 and 56, and an electroacoustic receiver 58 which includes piezoelectric material 60 sandwiched between a pair of electrodes 62 and 64. Again, transducers other than the piezoelectric type can be utilized. The transmitter 50 and the receiver 58 are spaced apart a known and fixed reference distance "$D_R$". The electrodes 62 and 64 are coupled to the input of the amplifier 66, whose output is coupled to the input of the detector 68. The output of the detector 68 is coupled to the pulse former 70 which generates trigger pulses. The trigger pulses are applied to the pulse generator 72 which controls the modulator 74 to pass bursts from the continuous wave oscillator 76 to the transmitter 50. The trigger pulses from the pulse former 70 are also applied to the counter 78.

Preferably, all of the transducers 16, 18, 50 and 58 have the same resonant frequency. Therefore, the oscillators 42 and 76 both operate at that frequency and the pulse generators 40 and 72 provide equal width output pulses.

In usage, the measuring unit 10 and the reference unit 12 are in close proximity so that the sound velocity in both of the units is the same. Although the repetition rates of the pulses in the measuring unit 10 and the reference unit 12 are each temperature and humidity dependent, it can be shown that the distance D to be measured is related to the reference distance $D_R$ as follows:

$$i \; D = D_R(1/t_R)/(1/t)$$

where $t_R$ is the propagation time over the distance $D_R$ in the reference unit 12. This relationship is independent of both temperature and humidity.

Thus, the outputs of the counters 46 and 78 are provided as inputs to the microprocessor 90 in the utilization means 14. The microprocessor 90 is appropriately programmed to provide an output which is proportional to the ratio of the outputs of the counters 46 and 78, which in turn are proportional to the repetition rates of the respective trigger pulse trains of the measuring unit 10 and the reference unit 12. As described, this ratio is independent of temperature and humidity and, since the reference distance $D_R$ is known, provides an accurate representation of the distance D. The utilization means 14 further includes a display 92 which is coupled to and controlled by the microprocessor 90 so that an operator can readily determine the distance D.

Experiments have shown that when the distance between the transmitting and receiving transducers is too small, reflections of the acoustic wave at the transducer surfaces has a not insignificant effect which degrades the measurement accuracy. Accordingly, it is preferred that each transducer pair be separated by at least a certain minimum distance, preferably about four inches.

Accordingly, there has been disclosed improved apparatus for the measurement of distance utilizing ultrasonic waves. While an illustrative embodiment of the present invention has been disclosed herein, it is understood that various modifications and adaptations to the disclosed embodiment will be apparent to those of ordinary skill in the art and it is intended that this invention be limited only by the scope of the appended claims.

What is claimed is:

1. Ultrasonic distance measuring apparatus comprising:

a reference unit including:

a reference electroacoustic transmitter responsive to an electrical pulse applied thereto for generating an acoustic wave having the resonant frequency of an apparatus transducer;

a reference electroacoustic receiver spaced a fixed reference distance from said reference transmitter, said reference receiver being responsive to said acoustic wave impinging thereon for generating an electrical signal;

reference feedback means coupled between said reference receiver and said reference transmitter and adapted to respond to an electrical signal from said reference receiver for applying a shaped electrical pulse to said reference transmitter; and reference pulse counting means coupled to said reference feedback means for providing a count of the number of pulses applied to said reference transmitter;

a measuring unit including:

a measuring electroacoustic transmitter responsive to an electrical pulse applied thereto for generating said acoustic wave;

a measuring electroacoustic receiver spaced from said measuring transmitter by a distance to be measured, said measuring receiver being responsive to said acoustic wave impinging thereon for generating an electrical signal;

measuring feedback means coupled between said measuring receiver and said measuring transmitter and adapted to respond to an electrical signal from said measuring receiver for applying a shaped electrical pulse to said measuring transmitter; and measuring pulse counting means coupled to said measuring feedback means for providing a count of the number of pulses applied to said measuring transmitter; and utilization means coupled to said reference and measuring pulse counting means for utilizing the ratio of the pulse counts of said reference and measuring pulse counting means to determine the distance between said measuring transmitter and receiver; whereby said apparatus is insensitive to temperature and humidity variations.

2. The apparatus according to claim 1 wherein each of said reference and measuring feedback means includes:

pulse generation means having an input and an output, said pulse generation means being responsive to an electrical signal at said pulse generation means input for providing a shaped electrical pulse at said pulse generation means output;

amplification means having an input coupled to the respective receiver and an output coupled to the respective pulse generation means input; and means for coupling said pulse generation means output to the respective transmitter.

3. The apparatus according to claim 2 wherein each of said pulse generation means includes:

trigger pulse generating means coupled to said amplification means output and responsive to the output from said amplification means being greater than a predetermined threshold value for generating a trigger pulse;

oscillator means for providing a continuous oscillating signal at a fixed frequency;

controllable modulation means coupled between said oscillator means and the respective transmitter; and control pulse generation means coupled between said trigger pulse generating means and said modulation means and responsive to said trigger pulse for applying a control pulse to said modulation means to cause said modulation means to pass said oscillating signal from said oscillator means to the respective transmitter.

4. The apparatus according to claim 3 wherein said control pulse generation means is effective to cause said modulation means to pass a predetermined number of cycles of said continuous oscillating signal.

5. The apparatus according to claim 3 wherein each of said counting means is coupled to receive trigger pulses from the respective trigger pulse generating means.

6. The apparatus according to claim 1 wherein said utilization means includes a microprocessor.

7. The apparatus according to claim 6 wherein said utilization means further includes a display coupled to and controlled by said microprocessor.

8. The apparatus according to claim 1 wherein each of said reference and measuring transmitters and receivers includes piezoelectric material sandwiched between a respective pair of electrodes.

* * * * *